(12) United States Patent
Kamal (10) Patent No.: US 10,639,050 B2
(45) Date of Patent: May 5, 2020

(54) SYSTEM AND METHOD FOR INTEROSSEOUS LIGAMENT RECONSTRUCTION

(71) Applicant: Robin Kamal, Palo Alto, CA (US)

(72) Inventor: Robin Kamal, Palo Alto, CA (US)

( * ) Notice: Subject to any disclaimer, the term of this patent is extended or adjusted under 35 U.S.C. 154(b) by 311 days.

(21) Appl. No.: 15/722,671

(22) Filed: Oct. 2, 2017

(65) Prior Publication Data

US 2019/0099192 A1 Apr. 4, 2019

(51) Int. Cl.
| | | |
|---|---|---|
| *A61B 17/17* | (2006.01) |
| *A61B 17/58* | (2006.01) |
| *A61F 2/08* | (2006.01) |
| *A61F 2/28* | (2006.01) |
| *A61B 17/72* | (2006.01) |

(52) U.S. Cl.
CPC ........ *A61B 17/1782* (2016.11); *A61F 2/0811* (2013.01); *A61F 2/28* (2013.01); *A61B 17/7291* (2013.01)

(58) Field of Classification Search
CPC ....... A61B 17/17; A61B 17/1782; A61F 2/28; A61F 2/08; A61F 2/0811
USPC ..................................................... 606/96–98
See application file for complete search history.

(56) References Cited

U.S. PATENT DOCUMENTS 3,664,022 A 5/1972 Small
4,159,716 A * 7/1979 Borchers ............ A61B 17/1682
606/104
4,920,958 A 5/1990 Walt et al.
4,945,904 A * 8/1990 Bolton ............... A61B 17/1714
606/96

(Continued)

FOREIGN PATENT DOCUMENTS

DE 19811354 A1 9/1999

OTHER PUBLICATIONS

Imex Universal Aiming Device dated Jun. 5, 2017, http://www.imexvet.com/products/product/universal-aiming-device, 1 p.

(Continued)

*Primary Examiner* — Jessica Weiss
(74) *Attorney, Agent, or Firm* — Knobbe, Martens, Olson & Bear, LLP (57) ABSTRACT

A method for interosseous ligament reconstruction (e.g., of a scapholunate or lunotriquetral ligament) includes drilling holes through both of the bones to allow for a graft to be placed on the volar and dorsal aspects of the bones, replicating the normal anatomic structure of the interosseous ligament, while requiring only an incision on the dorsal side of the wrist. The method includes using a drill guide that directs the drill to place a drill hole from dorsal to volar (front to back) in the bone, while making sure the drilled hole is within the joint on the volar side. The drill guide includes a hollow guide tube to advance a drill through, the hollow tube movably coupled to a shaft of the drill guide with a distal end that generally aligns with the distal end of the hollow tube. The shaft can have a sharp end that the drill will meet if passed through the drill guide, the sharp end of the drill guide being either hollow or solid, and can serve to release part of the wrist capsule (volar extrinsic carpal ligaments) from the bone in order to keep the drill hole within the wrist joint (and not outside of the joint).

4 Claims, 5 Drawing Sheets

(56) References Cited

U.S. PATENT DOCUMENTS

| | | | |
|---|---|---|---|
| D332,141 S * | 12/1992 | Rosenberg | D24/133 |
| 5,312,412 A * | 5/1994 | Whipple | A61B 17/1782 |
| | | | 606/105 |
| 5,688,283 A * | 11/1997 | Knapp | A61C 1/084 |
| | | | 433/75 |
| 5,725,532 A | 3/1998 | Shoemaker | |
| 7,060,068 B2 | 6/2006 | Tromanhauser et al. | |
| 7,299,561 B2 | 11/2007 | Castaneda | |
| 8,100,910 B2 | 1/2012 | Warburton | |
| 8,979,850 B2 | 3/2015 | Johnstone | |
| 9,095,440 B2 | 8/2015 | Orbay et al. | |
| 9,370,386 B2 | 6/2016 | Galm et al. | |
| 9,463,034 B2 | 10/2016 | Wong et al. | |
| 9,662,221 B2 | 5/2017 | Surma et al. | |
| 2009/0149858 A1 * | 6/2009 | Fanelli | A61B 17/1764 |
| | | | 606/80 |
| 2009/0306675 A1 * | 12/2009 | Wong | A61B 17/1703 |
| | | | 606/96 |
| 2012/0123417 A1 * | 5/2012 | Smith | A61B 17/1714 |
| | | | 606/80 |
| 2015/0313640 A1 | 11/2015 | O'Daly et al. | |

OTHER PUBLICATIONS

Innomed Argintar Claw Drill Guide Wire/Suture Passer dated Jun. 5, 2017, http://www.innomed.net/smallbone_handwrist_othertools.htm#ArgintarClawHandTools, 2 pp.

* cited by examiner

SYSTEM AND METHOD FOR INTEROSSEOUS LIGAMENT RECONSTRUCTION

BACKGROUND

Field

The present invention relates to surgical reconstruction of ligaments in a human wrist, and more particularly to systems and methods for reattachment of interosseous ligaments such as the scapholunate ligament or lunotriquetral ligament.

Description of the Related Art

The human wrist is a passive joint which relies on the articular surface of the bone and the interosseous ligaments to provide stability and allow for mobility of the wrist. The proximal carpal row, consisting of the scaphoid, lunate, and triquetrum, is the most common location of ligament tears in the wrist. These ligaments include the scapholunate ligament connecting the scaphoid and lunate bones, and the lunotriquetral ligament, connecting the lunate and triquetrum bones.

Scapholunate ligament and lunotriquetral ligament injury allows the two respective bones to move apart and leads to dysfunction and abnormal motion of the wrist. This can typically be seen by either a gap between the bones or an abnormal posture of the bones on x-rays. The width of the gap and the abnormality of the posture can vary between individuals. However, the motion of the bones becomes abnormal in all patients, causing pain, weakness, and leading to arthritis of the wrist if left untreated.

Multiple techniques for surgical reconstruction of the scapholunate ligament are known in the art. These techniques typically involve either reconstructing the ligament using nearby tissue in the back of the wrist, placing a screw or screw-like device (from one bone to the next, such as from the scaphoid bone across to the lunate bone) to connect the two bones, or placing a suture anchor through the bones to pass a tendon through the central axis of the two bones. These reconstructions are sometimes supported with wires placed between the two bones to hold them together temporarily. These reconstructions have overall mixed results with high rates of failure and wrist stiffness.

The existing techniques used for reconstruction of such ligaments as the scapholunate ligament and lunotriquetral ligament have several drawbacks, including: 1) they do not recreate the normal anatomy of the volar and dorsal (front and back) parts of the ligament, 2) they place a device or graft through the central axis of the two bones, which has been shown to not be anatomic and leads to abnormal kinematics (motion) of the wrist bones, and 3) they do not recreate the native ligament at all in the case of screw or screw-like reconstructions. Additionally, some existing reconstruction techniques also require making an incision on both the volar and dorsal sides of the wrist to release or disrupt the volar ligaments before holes are drilled through the wrist bones. Such holes are drilled through the bone without a guide from the dorsal incision, instead requiring multiple incisions and increased care from the surgeon to ensure the holes are drilled in the desired orientation.

SUMMARY

In accordance with one aspect, instrumentation and/or technique for interosseous ligament reconstruction (e.g., of a scapholunate or lunotriquetral ligament) is provided that includes making an incision only on the dorsal side of the wrist, and includes drilling holes through adjacent bones to allow for placement of a graft on the volar and dorsal aspects of the bones to replicate the normal anatomic structure of the interosseous ligament, while ensuring the drilled holes are within the joint on the volar side. The graft material and/or suture can be passed from dorsal to volar sides through the carpal bones (or volar to dorsal) and then can be either tied, sutured, or held in place (e.g., by using a bone anchor).

In accordance with one aspect, a drill guide for use in interosseous ligament reconstruction can include a hollow tube to place a drill through, the hollow tube being movable relative to a shaft laterally spaced from the hollow tube, where distal ends of the hollow tube and shaft are axially spaced apart and define an adjustable opening that receive a human wrist therein. The distal ends of the hollow tube and shaft are placed against the bone when drilling through the wrist bone. Optionally, the drill guide can have a sharp end in the shaft that the drill will meet if passed through the hollow tube. The sharp end of the shaft can be either hollow or solid, and can serve to release part of the wrist capsule (volar extrinsic carpal ligaments) from the bone in order to keep the drilled hole within the wrist joint (and not outside of the joint).

In accordance with another aspect, a drill guide for use in interosseous ligament reconstruction of a wrist is provided. The drill guide comprises a monolithic shaft having a proximal portion that extends along a central axis the shaft and a curved distal portion that extends to a distal end. The distal end includes a pointed lateral edge defined by an acute or right angle between a distal edge of the distal end and a circumferential side surface of the distal end, and a medial edge defined by an obtuse or right angle between the distal edge of the distal end and the circumferential side surface of the distal end. The distal edge is defined by a plane that extends substantially perpendicular to the central axis of the shaft. The drill guide also comprises a monolithic hollow tube extending along a central axis from a proximal end to a distal end and having a bore configured to receive a drill bit therethrough. The hollow tube is laterally spaced apart from the shaft, the distal end of the hollow tube axially spaced from the distal end of the shaft to define an adjustable opening therebetween configured to receive a human wrist therein. The hollow tube is movably coupled relative to the shaft and selectively movable by a user to adjust the size of the opening about the user's wrist such that the distal end of the hollow tube contacts a dorsal side of a wrist bone and the distal edge of the shaft is positionable proximal a volar side of the wrist bone. The pointed lateral edge of the distal end of the shaft is actuatable by a user to release ligaments from the volar side of the wrist bone to allow the drill bit to be extended through the hollow tube and through the wrist bone to the distal edge of the shaft while avoiding ligaments and nerves on the volar side of the wrist.

In accordance with another aspect, a method for interosseous ligament reconstruction of a wrist is provided. The method comprises making an incision on a dorsal side of the wrist, securing a drill guide about the wrist so that a distal end of a hollow tube is adjacent the dorsal side of a wrist bone and so that a distal edge of a shaft is proximal a volar side of the wrist bone, and extending a drill bit through the hollow tube and the wrist bone to the distal edge of the shaft to drill a hole through the wrist bone. The method also comprises repositioning the drill guide about the wrist so that the distal end of the hollow tube is adjacent the dorsal side of an adjacent wrist bone and so that the distal edge of the shaft is proximal a volar side of the adjacent wrist bone, and extending the drill bit through the hollow tube and the adjacent wrist bone to the distal edge of the shaft to drill a hole through the adjacent wrist bone. The method also comprises passing a graft or suture material through the hole in the wrist bone from the dorsal side to the volar side, then through the hole in the adjacent wrist bone from the volar side to the dorsal side, bringing the wrist bone and adjacent wrist bone together into their normal anatomic position, fixing the ends of the graft or suture material to create a closed circle or loop of the graft/suture, and closing the incision on the dorsal side of the wrist.

DETAILED DESCRIPTION

Figure 1A:
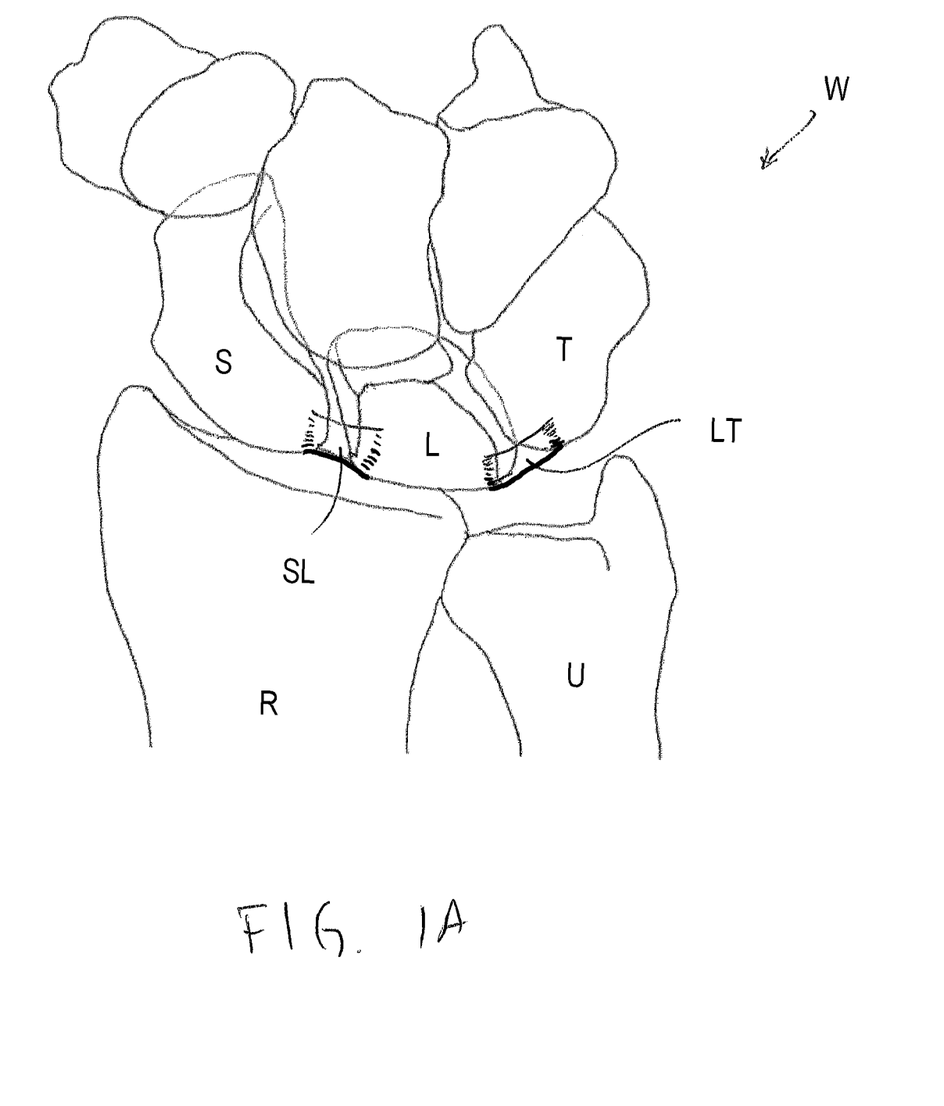
FIG. 1A is a schematic representation of a dorsal view of a wrist anatomy in a human right hand, showing the location of the scapholunate and lunotriquetral ligaments.
Figure 1B:
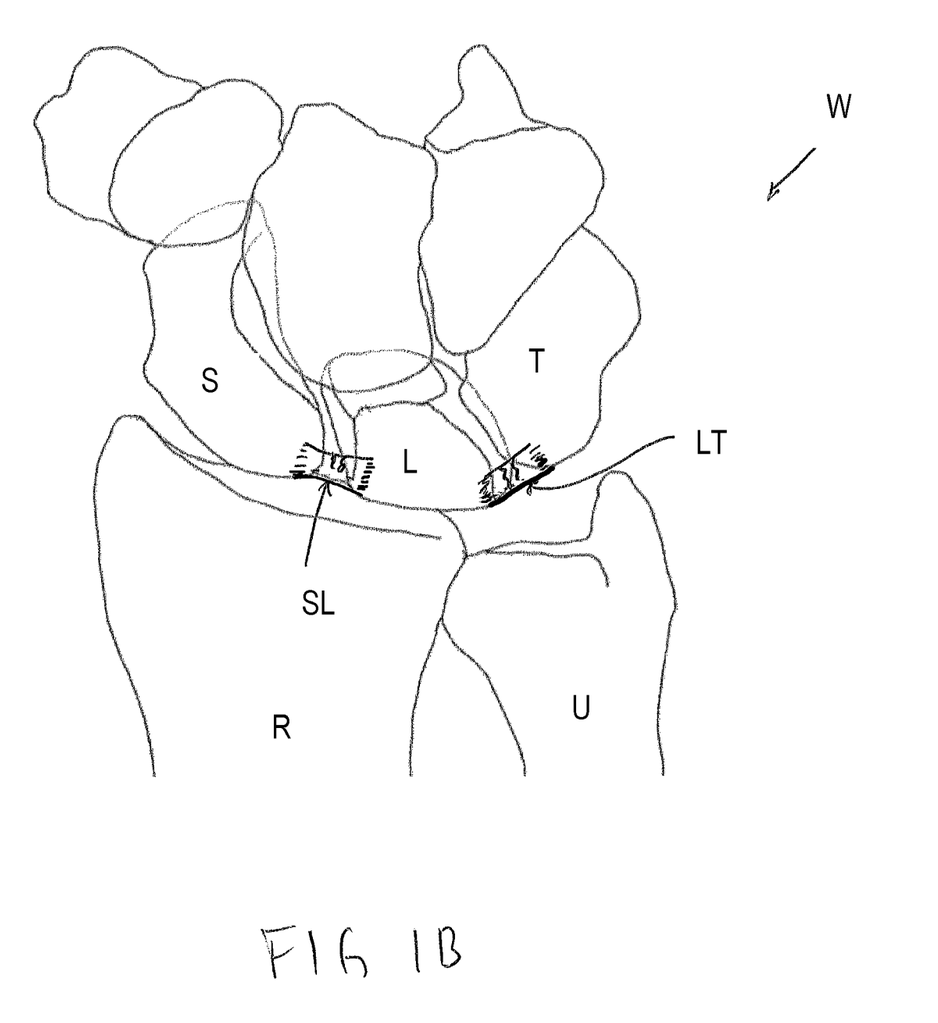
FIG. 1B shows the schematic representation of the dorsal view of the wrist anatomy in FIG. 1A showing tears in the scapholunate and lunotriquetral ligaments.

FIG. 1A shows a schematic representation of a dorsal view or aspect of a wrist W anatomy of a human right hand, showing the scaphoid S, lunate L and triquetrum T bones above the radius R and ulna U bones, with the scapholunate ligament SL extending between and connecting the scaphoid S and lunate L bones, and the lunotriquetral ligament LT extending between and connecting the lunate L and triquetrum T bones. FIG. 1B shows the wrist anatomy of FIG. 1A illustrating tears in the scapholunate and lunotriquetral ligaments SL, LT. Though only the dorsal side of the ligaments SL, LT are shown, one of skill in the art will recognize that the ligaments SL, LT are U shaped and wrap around the volar and dorsal sides of the bone, so the systems and methods described herein can be used to replace both the volar and dorsal sides of the ligaments SL, LT.

Figure 2:
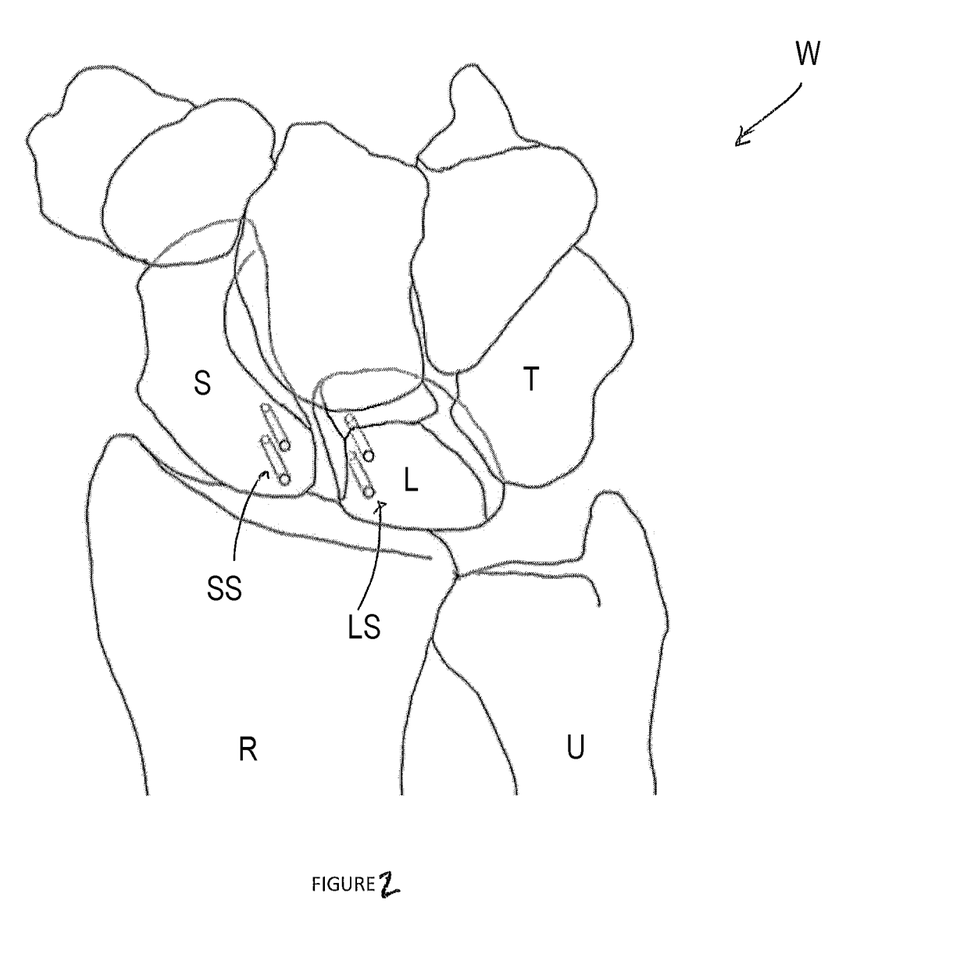
FIG. 2 shows the dorsal view of the wrist anatomy in FIG. 1A showing holes drilled into the scaphoid and lunate bones from dorsal to volar (from back to front).

FIG. 2 shows the wrist anatomy of FIG. 1A with one or more holes SS drilled into the scaphoid bone S and one or more holes LS drilled into the lunate bone L as part of a scapholunate ligament SL reconstruction procedure, further features of which are described below. Though FIG. 2 shows two holes SS in the scaphoid bone S and two holes LS in the lunate bone L, one skilled in the art will recognize that one hole can instead be drilled into each of the scaphoid S and lunate L bones.

Figure 3:
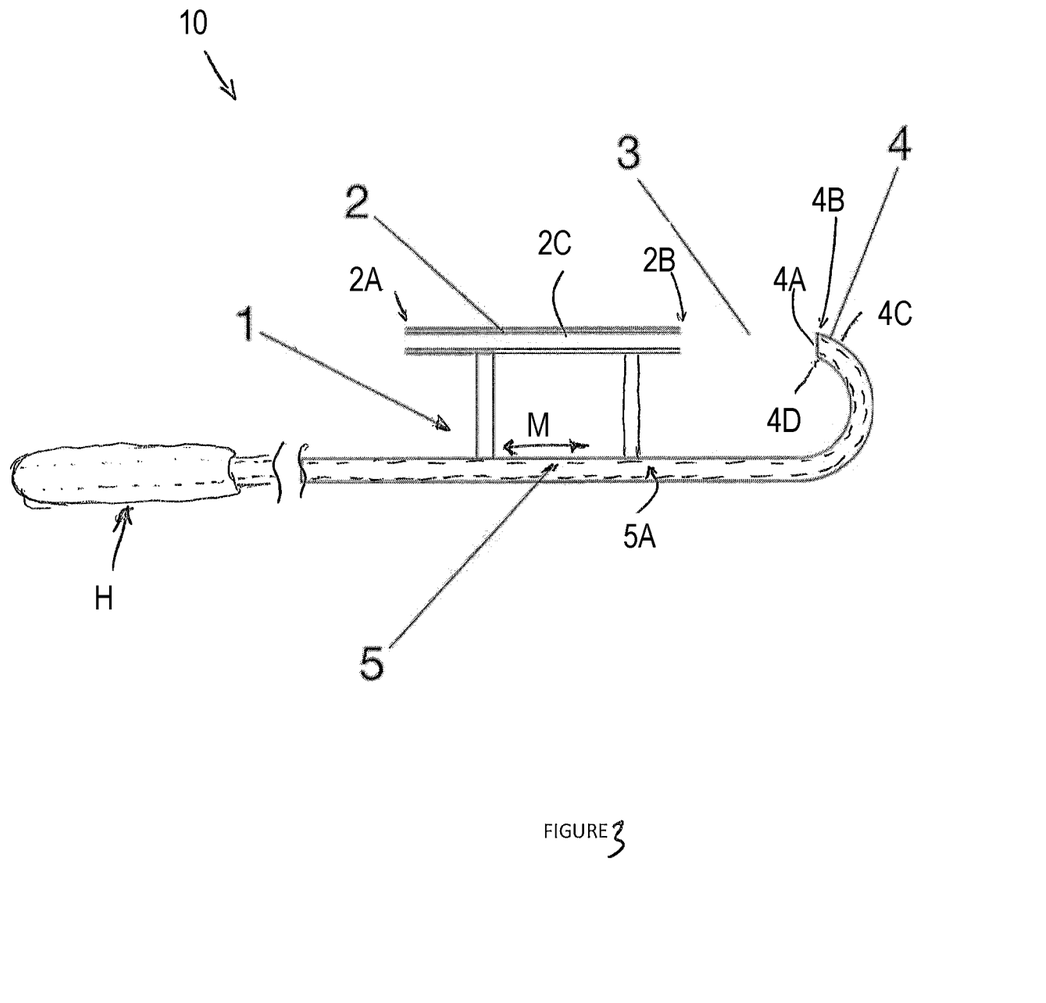
FIG. 3 is a schematic view of a drill guide used to form the holes in FIG. 2 in a surgical ligament reconstruction procedure

FIG. 3 shows a drill guide 10 for use in an interosseous ligament reconstruction procedure, such as a reconstruction of the scapholunate and lunotriquetral ligaments SL, LT in a human wrist W. The drill guide 10 includes a hollow tube 2 that extends linearly from a proximal end 2A to a distal end 2B and defines a bore 2C therethrough. The hollow tube 2 can be monolithic (e.g., seamless), such that it is defined as a single piece). The drill guide 10 also includes a shaft 5 that extends linearly from a handle H at a proximal end toward a distal portion 4. The shaft 5 and distal portion 4 can be monolithic (e.g., seamless), such that they are defined by a single piece. The distal portion 4 can be curved or hook-shaped, ending in a distal edge or surface 4A that optionally extends substantially perpendicular to the central axis of the shaft 5. The distal portion 4 can have other suitable shapes, such as L-shaped, U-shaped, etc. The distal edge or surface 4A joins an outer surface 4C of the distal portion 4 to define a pointed (e.g., sharp) lateral edge 4B defined by an acute angle (e.g., less than 90 degrees) between the distal edge or surface 4A and the outer surface 4C. The distal edge or surface 4A also joins the outer surface 4C of the distal portion 4 to define a medial edge 4D defined by an obtuse angle (e.g., more than 90 degrees).

Optionally, the shaft 5 is hollow from its proximal end through the distal portion 4, ending at the distal edge 4A. Alternatively, the shaft 5 is a solid shaft (i.e., not hollow) from its proximal end through the distal portion 4, ending at the distal surface 4A. The distal surface 4A can optionally be a flat surface.

Optionally, the distal end 2B of the hollow tube 2 aligns with the distal edge or surface 4A of the distal portion 4 of the shaft 5 so that a central axis of the hollow tube 2 is co-axial with a central axis of the distal edge or surface 4A. Alternatively, the hollow tube 2 extends along a central axis that is angled (i.e., not co-axial) relative to a central axis of the distal edge or surface 4A. The distal end 2B of the hollow tube 2 is spaced from the distal edge or surface 4A of the distal portion 4 of the shaft 5 and defines an opening 3 therebetween sized to receive a patient's wrist therethrough, as further discussed below. The size of the opening 3 (e.g., the distance between the distal end 2B of the hollow tube 2 is spaced from the distal edge or surface 4A of the distal portion 4) is variable and can be adjusted by the surgeon to allow the patient's wrist W to pass through the opening 3 and/or to secure the distal end 2B and distal edge or surface 4A against the wrist W.

The hollow tube 2 is spaced apart from the shaft 5, as shown in FIG. 3. Optionally, the central axis of the hollow tube 2 is parallel to the central axis of the shaft 5. The hollow tube 2 is movably coupled to the shaft 5 via one or more supports 1. Optionally, the one or more supports are fixed to the hollow tube 2 and movably coupled to the shaft 5. Alternatively, the one or more supports are fixed to the shaft 5 and movably coupled to the hollow-tube 2. Any suitable sliding mechanism can be used for movably coupling the hollow tube 2 to the shaft 5. For example, a ratchet and pawl system can selectively allow movement of the hollow tube 2 along the direction M to vary the size of the opening 3. In another example, a gear assembly can movably couple the hollow tube 2 and support(s) 1, or the shaft 5 and support(s) 1, and can be selectively operated via a rotating handle by the surgeon to move the hollow tube 2 relative to the shaft 5. Other mechanisms (e.g., T-slot slider, T-slot roller) can be used.

With continued reference to FIG. 3, the guide 10 can have one or more portions that are radiolucent (e.g., made of radiolucent material(s)) and/or one or more portions that are radiopaque (e.g., made of radiopaque material(s)). For example, the distal end 2B of the hollow tube 2 and the distal edge or surface 4A can optionally be radiopaque so that they can be seen under fluoroscopy. Optionally, other portions of the guide 10 can be radiolucent so that they are not visible under fluoroscopy.

Figure 4:
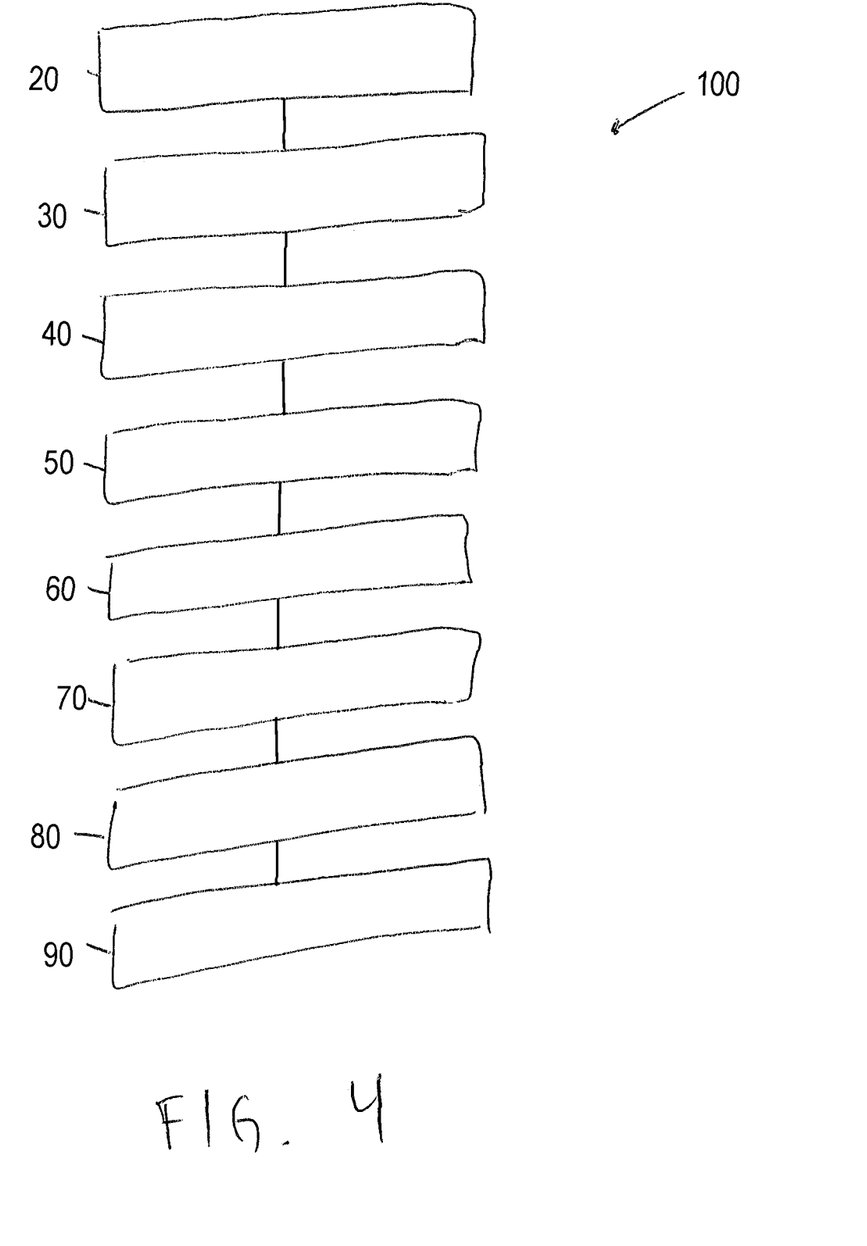
FIG. 4 is a block diagram illustrating a method of reconstructing an interosseous ligament in a human wrist.

FIG. 4 shows a block diagram of a method 100 for reconstructing an interosseous ligament in a human wrist, such as a scapholunate or lunotriquetral ligaments SL, LT. The method 100 includes one or more of the steps described herein.

The method 100 can include making an incision 20 in the dorsal side of the wrist W. The method 100 can optionally include inserting 30 controlling wires into the scaphoid S and the lunate L bones if reconstructing a scapholunate ligament SL (or into the lunate L and triquetrum T bones if reconstructing a lunotriquetral ligament LT). The method 100 can also include securing 40 the drill guide 10 about the wrist W so that the distal end 2B of the hollow tube 2 is adjacent the dorsal side of the bone (e.g., the scaphoid S, lunate L, or triquetrum T) and so that the distal edge or surface 4A of the distal portion 4 is placed proximal the volar side of the same bone. Securing 40 the drill guide 10 can optionally include one or more of: centering the drill guide 10 about the bone (e.g., scaphoid S, lunate L, triquetrum T), confirming the position of the guide 10 (e.g., the position of radiopaque distal end 2B and distal edge or surface 4A) under fluoroscopy, and sliding the hollow tube 2 relative to the shaft 5 to adjust the opening 3 so that the distal end 2B of the hollow tube 2 is locked against the dorsal side of the bone and the distal edge or surface 4A is locked proximal the volar side of the same bone. Securing 40 the drill guide 10 can also optionally include releasing the wrist capsule (e.g., volar extrinsic carpal ligaments) from the volar wrist bones (e.g., pushing the ligaments off the bone through tactile feel) to ensure the drilled hole is within the wrist joint and not outside the joint (e.g., to avoid ligaments and nerves on the volar side).

With continued reference to FIG. 4, the method 100 can also include extending a drill bit (e.g., cannulated drill bit) through the hollow tube 2 to drill 50 one or more holes SS, LS in each of the scaphoid S and lunate L bones if reconstructing a scapholunate ligament SL (or one or more holes in each of the lunate L and triquetrum T bones if reconstructing a lunotriquetral ligament LT) from the dorsal (front) side to the volar (back, palmar) side of the bones. Optionally, prior to drilling the holes, the method can include advancing a sleeve through the hollow tube 2 to the dorsal (front) side of the bones, and passing a wire at least partially into the bone to confirm the orientation of the wire is desirable, and then advancing a cannulated drill bit over the wire. Drilling 50 said one or more holes SS, LS can include forming the holes in each bone S, L in a position that brings the two bones together into their normal anatomic position when the graft and/or suture is passed through the bones. Drilling 50 said one or more holes SS, LS optionally includes extending the drill bit through the bone until the end of the drill bit contacts the distal surface 4A of the distal portion 4 (if the shaft 5 is solid) or until the end of the drill bit extends through the opening defined by the distal edge 4A (if the shaft 5 is hollow). Additionally, drilling 50 said one or more holes SS, LS optionally includes drilling the holes while under fluoroscopy to confirm the trajectory of the drill bit and to optionally view advancement of drill through the bone S, L and know once the hole(s) have been drilled through the volar side of the bone. Optionally, the surgeon holds onto the handle H of the drill guide 10 while advancing the drill bit through the hollow tube 2 to form the holes SS, LS.

The method 100 can also include passing 60 an autograft, allograft, xenograft, or synthetic material (e.g., suture material) from dorsal to volar in a wrist bone (e.g., the scaphoid S), then from volar to dorsal in the adjacent wrist bone (e.g., the lunate L) to recreate the volar and dorsal parts of the normal ligament in the wrist W. Optionally, passing 60 the graft material includes passing it through one or both of the hollow tube 2 and the shaft 5 (when the shaft 5 is hollow). For example, after the drill is withdrawn from the hollow tube 2 once all holes have been formed in the adjacent bones (e.g., scaphoid S and lunate L), the graft material can be delivered (using a needle) through the hollow tube 2 into the dorsal side of the bone and extended through the hole to the volar side of the bone, the distal surface of edge 4A can redirect the needle to the volar opening of the hole in the adjacent bone and the needle extended from volar to dorsal sides of the adjacent bone. In another example, the graft can be delivered through the hollow shaft 5 and out of the distal edge 4A, through the volar opening of the hole in a bone toward the dorsal side and once through the dorsal side, the needle can be redirected through the hole in the adjacent bone toward the volar side of said bone.

With continued reference to FIG. 4, the method can also include bringing 70 the two adjacent bones together. Optionally, this includes pulling the two ends of the graft material together to bring the adjacent bones together. Alternatively, the adjacent bones (e.g., scaphoid and lunate) are manually brought into their normal anatomic positions by the surgeon and held in such position with a temporary wire. The method can also include tying, suturing or otherwise fixing 80 the ends of the graft to create a closed circle or loop of the graft. Optionally, the graft can be fixed to itself, the dorsal capsule, or to the scaphoid/lunate with suture or with a suture anchor (e.g., a screw). Finally, the method includes suturing or otherwise closing 90 the incision on the dorsal side of the wrist W.

Advantageously, the method 100 includes only making one incision in the wrist W—on the dorsal side of the wrist W, in contrast to existing procedures that require making an incision on the volar side as well in order to disrupt the volar ligaments. The sharp lateral edge 4B of the distal portion 4 of the shaft 5 advantageously allows the release of the volar capsule (e.g., release or pushing the volar ligaments off the volar bones, via tactile feel) to ensure the drilled holes remain with the bones of the joint while avoiding the ligaments and nerves on the volar side. Additionally, the method 100 recreates the volar and dorsal (front and back) parts of the ligament using a drill guide as described above that directs the drill through the carpal bone, but keeps the drill holes within the wrist joint, and not through or outside of the wrist capsule or extrinsic carpal ligaments.

The method 100 and drill guide 10 described above are described in connection with the reconstruction of the scapholunate or lunotriquetral ligament, and is particularly applicable to these ligament reconstructions as the space between these bones is exceptionally small and reconstruction requires recreating both the volar and dorsal (front and back) parts of the ligament. However, the method 100 and drill guide 10 may be applied to any interosseous ligament reconstruction, including collateral ligament reconstructions in the fingers or toes.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A drill guide for use in interosseous ligament reconstruction of a wrist, comprising:
   a monolithic shaft comprising a proximal end, a distal end defining a distal-most edge, a central axis, an elongated proximal portion that extends along the central axis of the shaft, and a curved distal portion that extends to the distal-most edge of the shaft, wherein the shaft is hollow along its entire length, wherein the entirety of the distal-most edge extends substantially perpendicular to the central axis of the shaft, and wherein the distal-most edge defines an opening configured to receive a drill bit therein;

a handle coupled to the proximal end of the shaft; and a monolithic hollow tube extending along a central axis from a proximal end to a distal end and having a bore configured to receive a drill bit therethrough, the hollow tube laterally spaced apart from the shaft by one or more supports, each of the one or more supports coupled to both the shaft and the hollow tube, the distal end of the hollow tube spaced apart from the distal-most edge of the shaft to define an adjustable opening therebetween configured to receive a human wrist therein, the hollow tube being movably coupled relative to the shaft by a sliding mechanism configured to allow the hollow tube to move in a direction parallel to the central axis of the shaft in order to vary a size of the adjustable opening, wherein the hollow tube is selectively movable by a user to adjust the size of the adjustable opening about the user's wrist such that the distal end of the hollow tube is configured to contacts a dorsal side of a wrist bone and the distal-most edge of the shaft is configured to be positioned proximal to a volar side of the wrist bone, and wherein the distal-most edge of the shaft is configured to be used to release ligaments from the volar side of the wrist bone so that the drill bit can be extended through the hollow tube and through the wrist bone to the distal-most edge of the shaft while avoiding ligaments and nerves on the volar side of the wrist.

2. The drill guide of claim 1, wherein one or both of the distal end of the shaft and the distal end of the hollow tube are made of a radiopaque material.

3. The drill guide of claim 2, wherein a remainder of the one or both of the shaft and the hollow tube are made of a radiolucent material.

4. The drill guide of claim 1, wherein the shaft is configured to receive a suture therethrough to direct the suture through one or more holes formed in the wrist bone.

* * * * *